United States Patent [19]

Varadaraj et al.

[11] Patent Number: 5,514,588
[45] Date of Patent: May 7, 1996

[54] SURFACTANT-NUTRIENTS FOR BIOREMEDIATION OF HYDROCARBON CONTAMINATED SOILS AND WATER

[75] Inventors: Ramesh Varadaraj, Flemington; Cornelius H. Brons, Washington; Jan Bock, Warren; Stanley J. Brois, Westfield, all of N.J.

[73] Assignee: Exxon Research and Engineering Company, Florham Park, N.J.

[21] Appl. No.: 354,985

[22] Filed: Dec. 13, 1994

[51] Int. Cl.$^6$ .............................. B09B 3/00; C12N 1/38; A61L 11/00
[52] U.S. Cl. ............ 435/262; 435/262.5; 435/264; 435/244; 435/248; 424/76.5; 424/76.6; 424/76.8; 549/365
[58] Field of Search ................ 435/262, 262.5, 435/264, 266, 244, 248; 424/76.5, 76.6, 76.8; 549/365

[56] References Cited

U.S. PATENT DOCUMENTS

| | | | |
|---|---|---|---|
| 3,779,940 | 12/1973 | Argabright et al. | 435/262 |
| 3,852,220 | 12/1974 | Kimmel et al. | 435/262 |
| 3,959,127 | 5/1976 | Bartha et al. | 435/262 |
| 4,033,937 | 7/1977 | Argabright et al. | 435/262 |
| 4,042,495 | 8/1977 | Marconi et al. | 435/262 |
| 4,108,681 | 8/1978 | Lawson et al. | 435/262 |
| 4,146,470 | 3/1979 | Mohan et al. | 435/262 |
| 4,230,562 | 10/1980 | Olivieri et al. | 435/262 |
| 4,382,873 | 5/1983 | Gatellier et al. | 435/262 |
| 4,414,333 | 11/1983 | Olivieri et al. | 435/262 |
| 4,623,468 | 11/1986 | Lepain et al. | 435/262 |
| 4,764,285 | 8/1988 | Robbins et al. | 435/262 |

FOREIGN PATENT DOCUMENTS 56-100805  8/1981  Japan.

Primary Examiner—Douglas W. Robinson
Assistant Examiner—Louise N. Leary
Attorney, Agent, or Firm—Joseph J. Dvorak

[57] ABSTRACT

The present invention provides for enhanced bioremediation of hydrocarbon contaminated soils and waters by treating soil or water with a composition comprising a phosphorous source, a diluent and a compound or mixtures thereof represented by the structural formula:

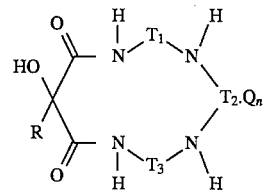

wherein R is a linear or branched alkane having about 8 to about 22 carbons, a linear or branched alkene having about 4 to about 22 carbon atoms; $T_1$, $T_2$, $T_3$ are independently ethylene, trimethylene, or $CH_2CH_2(NHCH_2CH_2)_x$, where x is an integer from 1 to 10; Q is $HNO_3$ or $H_3PO_4$; and, n is an integer from 0 to 10.

9 Claims, No Drawings

SURFACTANT-NUTRIENTS FOR BIOREMEDIATION OF HYDROCARBON CONTAMINATED SOILS AND WATER

FIELD OF INVENTION

This invention relates to surfactant-nutrient compounds suitable for enhancing the microbiological degradation of hydrocarbons in soils and water.

BACKGROUND OF THE INVENTION

It is well known that there are several microbial species found in soil and water that are capable of assimilating petroleum hydrocarbons. Unfortunately, the rate of microbial assimilation of petroleum hydrocarbons is relatively slow. It is necessary, therefore, to enhance the biological process if bioremediation is to be utilized in removing such pollutants from soils and water.

In general, the rate and extent of microbial utilization of petroleum hydrocarbons is limited by the concentration of microbial nutrients and microflora available at the hydrocarbon-water interface. Thus, microbial nutrients, especially nitrogen containing nutrients like urea and ammonium nitrate have been added to contaminated soil or water as a method for enhancing the biodegradation of the hydrocarbon contaminants. Because these nitrogen containing microbial nutrients are generally water soluble and because the petroleum hydrocarbons are hydrophobic, the nutrients are generally delivered in an aqueous solution, along with a surfactant which makes the contaminant bio-available to the hydrocarbon degrading microbes. Although this approach is useful, there remains a need for better approaches to making microbial nutrients bio available to the microbes at the hydrocarbon contaminant-water interface.

One object of the present invention therefore is to enhance the bioavailability of microbial nutrients by providing molecules that have surfactant and nutrient attributes.

Another object of the present invention is to provide a composition and method for stimulating the propagation of naturally occurring hydrocarbon assimilating microflora to enhance the bioremediation of hydrocarbon contaminated water and soils.

SUMMARY OF THE INVENTION

In one embodiment, the present invention comprises treating a hydrocarbon contaminated soil or water with a compound capable of reducing the interfacial tension between water and the hydrocarbon contaminant and selected from the group consisting of macrocyclic amido amines, macrocyclic amido amine acid salts and mixtures thereof.

In another embodiment of the present invention there is provided a composition useful in treating hydrocarbon contaminated soil or water comprising: a compound selected from the group consisting of macrocyclic amido amines, macrocyclic amido amine acid salts and mixtures thereof; a phosphorous source; and a liquid diluent.

These and other embodiments of the invention will be described in detail hereinafter.

DESCRIPTION OF THE PREFERRED EMBODIMENTS

The present invention provides for enhanced bioremediation of hydrocarbon contaminated soils and waters by treating the soil or water with a microbial assimilable surfactant-nutrient compound selected from the group consisting of macrocyclic amido amines, macrocyclic amido amine acid salts and mixtures thereof.

The preferred macrocyclic amido amine and their acid salts are represented by the structural formula:

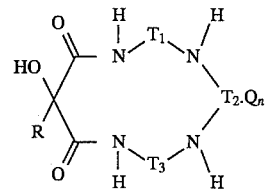

where R is selected from linear or branched alkanes with 8 to 22 carbons, linear or branched alkenes with 4 to 22 carbons; $T_1$, $T_2$ and $T_3$ are independently selected from ethylene, trimethylene, $CH_2CH_2(NHCH_2CH_2)_x$ where x is an integer from 1 to 10; Q is $HNO_3$ or $H_3PO_4$ and n is an integer from 0 to 10.

As will be described more fully, the macrocyclic amido amines useful in the present invention are readily prepared by condensing polyamines with ene and radical adducts of vicinyl tricarbonyl compounds. The acid salts are easily prepared by adding acid to the amido amine.

Ene adducts useful in the present invention can be prepared by contacting an unsaturated hydrocarbon having from 4 to 22 carbon atoms with a vicinyl tricarbonyl compound, especially a cyclic vicinyl tricarbonyl such as pyrimidine trione, at a temperature at which thermal ene addition occurs without appreciable decomposition. The reaction temperature will vary depending upon the particular unsaturated hydrocarbon that is employed. Generally, reaction temperatures within the range of from about 20° C. to about 200° C. are useful. Effective contacting of the olefin and tricarbonyl can be achieved by combining the reactants together with a solvent, or neat. The contacting is continued for a time sufficient to form the ene adduct.

Radical adducts of a vicinyl tricarbonyl such as pyrimidine trione are prepared by contacting an aliphatic hydrocarbon of from about 8 to about 22 carbon atoms with the carbonyl in the presence of a free radical initiator. Radical grafting of hydrocarbons is conveniently conducted without a solvent or diluent. For example, a neat hydrocarbon such as pristane, and about 2 wt. % (based on hydrocarbon weight) of pyrimidine trione are combined in a nitrogen-blanketed reactor, at about 160° C. Radical grafting is initiated by adding in one dose, about 1–100 wt. % (based on monomer weight) of a free radical initiator such as t-butyl peroxide, for example, and stirring the mixture at 160° C. until radical grafting is complete, thereby forming a radical adduct.

The foregoing ene and radical adducts are converted to macrocyclic amido amines useful in the present invention by condensing them with polyamines, such as 3,3'-amino-bis-propylamine, diethylene-triamine, triethylene tetraamine, 1,3-bis-(2-aminoethyl)-1,3 propanediamine, tetraethylene-pentamine and polyamine-H (a mixture of higher ethylene amines including pentaethylene-hexamine). The condensation typically is conducted in a solvent such as dioxane at a temperature in the range of from about 25° C. to about 100° C., and preferably at about 60° C. for a time sufficient to form the macrocyclic amido amine. Typically this requires several hours, e.g., from about 5 to about 8 hours.

Addition of one or more moles of a mineral acid such as nitric or phosphoric acid, to a macrocyclic amidoamine affords the corresponding salt derivative. Salt formation can be readily carried out by combining the reactants together neat or in a solvent.

An important aspect of the present invention is the fact that the described surfactant macrocyclic amido amines speed up the natural process of biological degradation by performing two functions: (1) increasing the interface between the hydrocarbon contaminant in the soil or water, the microflora and nutrients and (2) stimulating propagation of the microflora by supplying microbial nutrients at the interface.

Specific illustrative examples of surfactant macrocyclic amido amines having the formula shown below which are useful in the present invention are given in Table 1

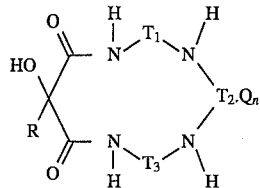

TABLE 1

| Example | Formula |
|---|---|
| 1. | T1 = T3 = Ethylene; T2 = Trimethylene; R = 2-Octadecenyl; n = 0 |
| 2. | As above in 1 but with Q = $HNO_3$ and n = 1 |
| 3. | As above in 1 but with Q = $HNO_3$ and n = 2 |
| 4. | As above in 1 but with Q = $H_3PO_4$ and n = 1 |
| 5. | T1 = T2 = T3 = Ethylene n = 0; R = 2-Octadecenyl |
| 6. | T1 = T3 = ethylene; T2 = trimethylene; n = 0; R = 2, 6, 10, 14- Tetra methyl pentadecane |

Key interfacial properties of some of these surfactant macrocyclic amido amines are given in Table 2.

In those instances when the surfactant is water dispersible a co-solvent may be employed. Suitable so-solvents include alcohols such as isopropyl alcohol.

When the surfactant is water insoluble, they can be delivered to the contaminated soil or water as a solution in a hydrocarbon solvent. Easily biodegradable low molecular weight petroleum distillates having a high normal paraffin content such as Norpar® solvents sold by Exxon Company USA, Houston, Tex., are especially preferred hydrocarbon solvents.

The macrocyclic compounds of the present invention are advantageously employed in combination with other microbial nutrients, especially a phosphorus source. For example, various compounds such as ammonium phosphate, trilaureth phosphate and alkyl phosphates are quite suitable for use in conjunction with the macrocyclic compounds of the present invention. In general, the macrocyclic compounds and phosphorous source are combined to provide a N:P weight ratio of about 10:1 to about 10:5. Additionally, the macrocyclic compounds of the present invention may be combined with a co-surfactant such as nonionic, anionic or cationic surfactants to provide added surfactancy, if desired. Thus, the present invention provides a composition useful in treating hydrocontaminated soil and water comprising a macrocyclic compound of the present invention, a phosphorous source, cosurfactants and a diluent.

Optionally, the composition may include micro nutrients such as sources of iron, copper, zinc, cobalt.

A preferred composition will contain from 10% to about 45% by weight of the macrocyclic compound and phosphorous source based on the total weight of the composition, with the balance being additional nutrients, co-surfactant if any and diluent.

The foregoing compositions are applied to soil or water at the rate of 5 wt. % to 3 wt. % of treat to hydrocarbon contaminant. The amount of treat is added to achieve a

TABLE 2

| Composition (Example of Table 1) | 1 | 2 | 3 | 4 |
|---|---|---|---|---|
| Interfacial property at 25° C. | | | | |
| Air-Water Interface[1] | | | | |
| Critical micelle concentration, CMC (M) | $2.5 \times 10^{-4}$ | $5 \times 10^{-4}$ | $2.5 \times 10^{-3}$ | $2.5 \times 10^{-3}$ |
| Surface tension at CMC (dynes/cm) | 41.0 | 35.3 | 39.9 | 42.3 |
| Hydrocarbon-Water Interface[2] | | | | |
| Interfacial tension against cyclohexane (dynes/cm) | 25 | 24.6 | 20.0 | 16.6 |
| Interfacial tension against toluene (dyes/cm) | 5.4 | 23.1 | 12.4 | 18.3 |
| Paraffin-Water Interface[3] | | | | |
| Contact Angle | | | | |
| Advancing (degrees) | 82 | 74 | 82 | 88 |
| Receding (degrees) | 49 | 33 | 54 | 51 |

[1]Air-water interfacial properties determined using the Wilhelmy plate method.
[2]Hydrocarbon-water interfacial tension determined by the pendant drop method.
[3]Parafilm-water contact angle determined by the dynamic contact angle method using a Cahn balance DCA analyzer.

In treating hydrocarbon contaminated soil or water with the macrocyclic amido amine, macrocyclic amido amine acid salt and mixtures thereof, it is preferred to deliver them i.e., broadcast, spray or the like, dispersed or dissolved in a solvent. Water is the preferred solvent for those surfactant amido amine compounds that are water soluble.

C:N:P ratio in the range 100:10:1 to 100:1:0.1, the preferred range being 100:2:0.2.

Example 7 and Comparative Examples 1 and 2

The biodegradation of an Alaskan North Slope crude oil 520°–1050° F. distillate cut was tested with a composition consisting of:
  (a) 20 wt. % macrocyclic amido amine 5 of Table 1 as the nitrogen source
  (b) 2.0 wt. % of a mixture of mono and dialkyl phosphates, specifically Emphos PS 400 sold by Witco Corporation, New York as the phosphorous source.
  (c) 4.5 wt. % of sorbitan mono oleate, specifically Span 80 sold by ICI Americas, Inc., Wilmington, Del., as co-surfactant.
  (d) 8.4 wt. % of sorbitan mono oleate ethoxylate, specifically Tween 80 sold by ICI Americas, Inc., Wilmington, Delaware as co-surfactant.
  (e) 16.8 wt. % of dioctyl sodium sulfo succinate, specifically Aerosol OT-75 sold by Cytec Industries, American Cyanamid, N.J., as co-surfactant
  (f) 13.0 wt. % of sorbitan trioleate ethoxylate, specifically Tween 85 sold by ICI Americas, Inc., Wilmington, Del. as co-surfactant.
  (g) 17.6 wt. % of n-tridecane, specifically Norpar-13 sold by Exxon Chemical Company, Houston, Tex. as solvent.
  (h) 17.5 wt. % and of dipropylene glycol n-butyl ether as solvent.

For these tests, 10 wt. % (Example 7) of the composition to oil (0.5 g) and 50 ml of $H_2O$ was used.

For comparative purposes, a control was run with no treatment (Comparative Example 1) as well as a run with urea as nitrogen source and $NH_4H_2PO_4$ as phosphorous source (Comparative Example 2). For Example 7 and Comparative Example 2 the C:N:P ratio was 100:0.5:0.04. The tests were conducted as follows:

Shake flask cultures for assay of the biological efficacy were set up in sterile 300 ml baffled flasks. Each flask contained 50 ml of a sterile mineral medium with 0.5 g of the Alaskan crude added. The surfactant-nutrient additive formulation was first thoroughly mixed with the crude oil before the mixture was added to the culture flask. Flasks were incubated at 25° C. Aeration was achieved by shaking at 200 RPM. Inoculation for biological activity was made at 10%, e.g., 10 ml of inoculum per 100 ml culture.

Inoculum for biological activity was provided using clarified sludge from process water biological oxidation unit of a commercial petroleum refinery. The inoculum was prepared by stirring approximately 900 ml of the sludge with aeration. After 24 hours, the aerated sludge was centrifuged and the pellet re-suspended in the mineral medium to generate the inoculum.

The percentage of hydrocarbon biodegraded was determined by gas chromatography after 120 hrs. of experiment. The results are given in the Table 3 below:

TABLE 3

| Example | % Hydrocarbon Biodegraded |
| --- | --- |
| Example 7 | 14% |
| Comparative Example 1 | <2% |
| Comparative Example 2 | 5% |

What is claimed is:

1. A composition comprising:
   a phosphorus source;
   a diluent; and,
   a compound selected from the group consisting of macrocyclic amido amines, macrocyclic amido amine acid salts, and mixtures thereof represented by the formula:

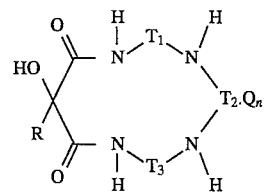

wherein R is a linear or branched alkane having about 8 to about 22 carbon atoms, a linear or branched alkene having about 4 to about 22 carbon atoms;

$T_1$, $T_2$ and $T_3$ are independently ethylene, trinethylene or $CH_2CH_2(NHCH_2CH_2)_x$ where x is an integer from 1 to 10;

Q is $HNO_3$ or $H_3PO_4$; and n is an integer from 0 to 10.

2. The composition of claim 1 wherein the phosphorous source is selected from the group consisting of ammonium phosphate, trilaureth phosphate and alkyl phosphates having 8 to 22 carbon atoms in the alkyl group, and mixtures thereof.

3. The composition of claim 2 wherein the macrocyclic compound and the phosphorous source are combined to provide a N:P ratio from about 10:1 to 10:5.

4. The composition of claim 3 wherein the diluent is selected from the group consisting of water, low molecular weight hydrocarbons, and water-alcohol mixtures.

5. The composition of claim 4 further including a co-surfactant selected from the group consisting of nonionic, anionic and cationic surfactants.

6. The composition of claim 5 wherein the macrocyclic compound and phosphorous source are present in an amount ranging from about 10% to about 45% by weight of the total weight of the composition.

7. A method for enhancing the biodegradation of hydrocarbon contaminated soil or water comprising:
   applying to the soil or water a compound selected from the group consisting of macrocyclic amido amines, macrocylic amido amine acid salts, and mixtures thereof having the formula:

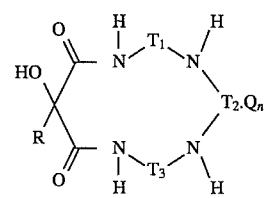

wherein R is a linear or branched alkane having about 8 to about 22 carbon atoms, a linear or branched alkene having about 4 to about 22 carbon atoms; $T_1$, $T_2$ and $T_3$ are independently ethylene, trimethylene, or $CH_2CH_2(NHCH_2CH_2)_x$, where x is an integer from 1 to 10; Q is $HNO_3$ or $H_3PO_4$; and, n is an integer from 0 to 10.

8. The method of claim 7 wherein the compound applied is combined with (a) a phosphorous source in an amount to provide an N:P ratio in the range of 10:1 to 10:5 and (b) a diluent selected from the group consisting of water, low molecular weight hydrocarbons, and water-alcohol mixtures.

9. The method of claim 8 wherein the compound and phosphorous sources are applied to the soil or water to provide a C:N:P ratio in the range of 100:10:1 to 100:1:0.1.

* * * * *